US005422241A

United States Patent [19]

Goldrick et al.

[11] Patent Number: 5,422,241

[45] Date of Patent: Jun. 6, 1995

[54] METHODS FOR THE RECOVERY OF NUCLEIC ACIDS FROM REACTION MIXTURES

[75] Inventors: Marianna Goldrick, Pfluegerville; Matthew Winkler, Austin, both of Tex.

[73] Assignee: Ambion, Inc., Austin, Tex.

[21] Appl. No.: 724,423

[22] Filed: Jul. 3, 1991

[51] Int. Cl.[6] .......................... C12N 9/22; C12N 9/99

[52] U.S. Cl. ........................................ 435/6; 435/184; 435/195; 935/77; 935/19; 536/25.4; 536/25.41; 536/25.42

[58] Field of Search .................................... 536/27-29, 536/25.4, 25.41, 25.42; 435/19, 270, 6, 184, 195, 77; 564/230

[56] References Cited

U.S. PATENT DOCUMENTS 4,843,155 6/1989 Chomczynski ...................... 536/27

OTHER PUBLICATIONS

Cox, R. A.: Methods in Enzymology 12(B):121-129, 1968.

Gilman, M., "Ribonuclease Protection Assay," Current Protocols in Molecular Biology, Wiley Interscience, vol. 1, Suppl. 7, pp. 4.7.1-4.7.8, 1989.

Sambrook et al., "Mapping of RNA with Ribonuclease and Radiolabeled RNA Probes," Molecular Cloning: A Laboratory Manual, Second Edition, Cold Spring Harbour Laboratroy Press, pp. 7.71-7.77, 1989.

Chomczynski, P. and Sacchi, N., "Single-Step Method of RNA Isolation by Acid Guanidinium Thiocyanate--Phenol-Chloroform Extraction," *Anal. Biochem.*, 162:156-159, 1987.

"Ambion Catalog #1400: RPA" Ribonuclease Protection Assay Kit Instruction Manual.

*Primary Examiner*—Douglas W. Robinson

*Assistant Examiner*—Gary L. Kunz

*Attorney, Agent, or Firm*—Arnold, White & Durkee

[57] ABSTRACT

A method for the recovery of nucleic acids from a reaction mixture, such as nuclease protection assays, comprising the use of one reagent containing a) nuclease for digesting single-stranded RNA and b) a nucleic acid precipitating carrier agent, (sheared DNA or linear acrylamide). A second reagent contains a chaotropic agent (a guanidinium salt) for inactivating said nucleases and an alcohol (ethanol or isopropanol) for the simultaneous inactivation of the nucleases and the precipitation of the nucleic acids without the need for protease digestion or organic extraction.

13 Claims, No Drawings

METHODS FOR THE RECOVERY OF NUCLEIC ACIDS FROM REACTION MIXTURES

BACKGROUND OF THE INVENTION

1. Field of the Invention

This invention relates to methods and compositions for carrying out certain enzymatic reactions, specifically, to the recovery of nucleic acid from in vitro reaction mixtures that contain nucleases.

2. Description of the Related Art

Extensive study of the molecular biology of gene expression has led to improved methods for detection and quantitation of the messenger ribonucleic acid (mRNA) found in cells and tissues. A common method of mRNA analysis, called nuclease protection assays or ribonuclease protection assays, is performed routinely in many academic and medical research labs according to standard protocols. The standard protocols include obligatory steps for the recovery of undegraded nucleic acid from experimental reaction mixtures that contain degradative nuclease enzymes. Investigators will welcome further improvements that streamline the process of performing nuclease protection assays.

Analysis of gene expression often starts with the isolation of RNA from cells or tissues. Some of the requirements for isolation of RNA from biological sources are also requirements for successful analysis of the RNA using the method of nuclease protection assays. Specifically, both processes require recovery of intact nucleic acid from mixtures that contain nucleases (enzymes which degrade nucleic acid). Because the two processes are intertwined, the prior art will be reviewed as it relates to both RNA isolation from biological sources and RNA recovery from in vitro reactions. Fundamental differences between the two processes will then be considered.

Many currently used protocols for isolation of RNA from biological sources involve disruption of cells or tissue in concentrated solutions of guanidinium thiocyanate to inactivate endogenous nucleases and shear DNA, followed by phenol/chloroform extraction to denature and remove proteins. The RNA is recovered after the addition of ethanol or isopropanol which causes it to precipitate out of solution. (Chomczynski, et al., 1987) Sometimes recovery of RNA is accomplished by CsCl gradient centrifugation as an alternative to, or in addition to, alcohol precipitation. Other ingredients are often added to the guanidinium solution to aid in the inactivation of the nucleases. Examples include detergents (usually N-lauroyl sarcosine), reducing agents (e.g., dithiothreitol, 2-mercaptoethanol), and chelating agents (e.g., EDTA).

A typical procedure for isolation of RNA from mammalian tissue is found in Current Protocols in Molecular Biology (Ausbel, et al., 1987). This procedure involves homogenizing the tissue in a solution of guanidinium thiocyanate, Tris buffer, and β-mercaptoethanol, centrifuging the suspension to remove particulate debris, adding N-lauroyl sarcosine, and sedimenting the RNA through a CsCl gradient by ultracentrifugation. The RNA pellet is resuspended in a solution of EDTA, N-lauroyl sarcosine, and β-mercaptoethanol and then extracted with an equal volume of phenol:chloroform:isoamyl alcohol. After extraction, the solution is adjusted to 0.3M sodium acetate and the RNA is precipitated by the addition of 2.5 volumes of ethanol. After overnight incubation at −20° C., the RNA is recovered by centrifugation.

For the inactivation of nucleases in ribonuclease protection assays, the method presently recommended in the literature involves treating the reaction mixture with proteinase K (a protease enzyme that degrades the nuclease) (Sambrook, et al., 1989). This is typically performed in the presence of the ionic detergent sodium dodecyl sulfate (SDS), followed by phenol/chloroform extraction. After this organic extraction, each reaction mixture in the assay series is transferred to a new microcentrifuge tube. Extraneous nucleic acid is frequently added to the reaction after the organic extraction to act as a carrier to aid in the quantitative precipitation of the RNA. The RNA is then recovered by alcohol precipitation, solubilized in a suitable buffer, and analyzed, usually by electrophoresis on thin polyacrylamide gels. A typical protocol for ribonuclease inactivation and recovery of RNA from a ribonuclease protection assay is given in *Molecular Cloning: A Laboratory Manual* (Sambook, et al., 1989).

Although the isolation of RNA from biological sources and recovery of RNA from nuclease protection assays are similar in some respects, there are more differences than similarities. For example, the protein concentration in nuclease protection assays is low, whereas during RNA isolation from cells or tissue, protein is present in much higher concentrations. Other contaminants present in the cell or tissue homogenates are polysaccharides, cell membranes, DNA and debris derived from organelles. These contaminants are not present in the in vitro nuclease protection reaction mixture. Thus, procedures for RNA isolation must include steps not only for nuclease inactivation, but also for selective removal of protein and other contaminants. In contrast, the removal of protein and other contaminants from in vitro nuclease protection assays is not required, since the only protein present is the nuclease itself.

Since the experimental basis for nuclease protection assays is the selective hybridization of the mRNA being detected to a specific complementary RNA or DNA probe, reaction conditions are chosen that maximize hybridization. Subsequent to the hybridization, the reaction is adjusted to allow nuclease digestion of unhybridized probe. Therefore, components of the in vitro hybridization and nuclease digestion reactions must be considered when the reaction is finally adjusted for the inactivation of the nucleases and recovery of the hybridized RNA. In contrast, the isolation of RNA from biological sources can be carried out in a reaction mixture that is optimized only for the selective recovery of intact RNA.

Nuclease protection assays require the quantitative recovery of small amounts of labeled RNA (usually radioisotopically labeled), while cellular RNA isolation involves selective recovery of unlabeled RNA from complex mixtures containing relatively high concentrations of RNA. To aid in the quantitative recovery of the small amount of RNA in the nuclease protection reactions, a carrier such as tRNA or yeast RNA is often added to increase the total RNA concentration.

From a practical standpoint, it is important that the procedure for recovery of RNA from in vitro nuclease protection assays be rapid and simple enough to permit the recovery of RNA from multiple samples (on the order of 10–20 samples), since many samples are usually analyzed in parallel. In contrast, while speed and simplicity are obvious advantages in procedures for cellular RNA isolation, they are not critical parameters since the RNA is usually being isolated from only one or a few sources.

By their nature, nuclease protection assays require the application of multiple steps. Innovations that make any of these steps less cumbersome and time consuming will enhance the usefulness of the assay and broaden its appeal. As previously performed, nuclease protection assays require the application of multiple steps which can be cumbersome and time consuming. For example, previous assays require the use of proteinase digestion and organic extraction to remove enzymes prior to RNA precipitation. Organic extraction is a step that involves a significant degree of handling and can result in a loss of desired nucleic acids into the organic phase. There is, in fact, an overall need to improve the efficiency of recovery of nucleic acids from protection assays. Such improvements could go a long way towards simplifying these assays, opening the possibility of automation and making them more readily practiced by less trained laboratory personnel, freeing such individuals to carry out other work.

SUMMARY OF THE INVENTION

The present invention involves the development of techniques that will allow, among other things, a faster and more efficient method for recovering nucleic acid from in vitro reaction mixtures that contain degradative nuclease enzymes. The invention will find particular applicability to use in connection with nuclease protection assays. The methods of the invention represent a substantial improvement over existing methods because a multi-step procedure requiring a proteinase digestion and organic extraction is replaced with an overall shorter protocol that circumvents both of these steps.

A particular aspect of the invention is the creation of two novel reagents for use at different stages of the experimental procedure. The first reagent incorporates into reaction procedures a special ribonuclease-resistant "carrier" that promotes the quantitative precipitation of nucleic acid upon the subsequent addition of alcohol to the reaction. This carrier is one that is essentially resistant to the action of nucleolytic action by the selected nucleases. (In that the carrier is normally not a protein, it will typically also be resistant to proteolytic action). The carrier serves to promote precipitation of minute amounts of RNA (e.g., on the order of 100 ng), which might otherwise remain in the supernatant fluid. Preferred carriers used in the previous practice of protection assays have included tRNA and total yeast RNA. However, the present inventors have found particular advantages to the use of a special carrier such as linear acrylamide, sheared DNA (e.g., sheared to a size of on the order of 50 to 5000 bases), or other carriers resistant to RNase digestion. The inventors prefer the inclusion of linear acrylamide at a concentration of 0.01 to 1 mg/ml (particularly 0.1 mg/ml) or sheared DNA at concentrations of 10 to 100 $\mu$g/ml (particularly 20 $\mu$g/ml).

For ease of use, the first reagent will also typically include suitable buffers (e.g., Tris base, Sigma T1503, HEPES, Sigma H3375, etc.) and salts (e.g., Na-citrate, NaCl, etc.) to promote and support nucleolytic action, as well as an amount of a ribonucleolytic enzyme effective to digest single-stranded RNA. Preferred enzymes include ribonucleases A and T1, particularly recombinant and preferably used in combination. However, other enzymes capable of digesting single-stranded RNA while leaving "protected" regions intact, such as RNase I, from *E. coli.*, or S1 nuclease, may be employed as appropriate. To further improve the reaction conditions, other agents such as EDTA, Sigma ED2SS, may optionally be included in the first reagent, or as an associated aliquot.

The inclusion of the special carrier in the digestion buffer represents an improvement over existing methods in that it eliminates the need to add a carrier separately, after inactivation of the nucleases. (The requirement for adding carrier separately in the standard method is due to the fact that the standard carrier, tRNA or yeast RNA, is ribonuclease sensitive and would thus be degraded before it could act to promote nucleic acid precipitation.) The use of ribonuclease-resistant linear acrylamide or fragmented DNA as a carrier therefore permits the experimental design to be streamlined.

In preferred embodiments, a second reagent is used for the simultaneous inactivation of nucleases and precipitation of nucleic acid. This reagent contains a guanidinium-based chaotropic compound, such as guanidinium thiocyanate or guanidinium chloride, as the primary nuclease inactivating agent. The reagent may further include a reducing agent such as dithiothreitol (DTT) or $\beta$-mercaptoethanol, and a detergent such as N-lauroyl sarcosine or SDS to further enhance nuclease inactivation. The second reagent also preferably contains an alcohol such as isopropyl alcohol or ethanol in a concentration optimized for precipitation of nucleic acid. Additional benefits may be realized through the inclusion of a chelating agent such as EDTA, or other suitable chelators known in the art. For convenience of use, other agents such as Na-citrate may also be included in the second reagent.

Addition of the second reagent in its most preferred embodiment to the nuclease protection reaction mixture simultaneously inactivates the nucleases present from the previous step and effects the precipitation of the nuclease-resistant hybridized duplex nucleic acid molecules. The second reagent thus replaces the proteinase K, SDS, phenol/chloroform, and ethanol that are commonly used in standard nuclease protection assays.

Exemplary specific embodiments of some aspects of the present invention may be described as follows. The invention includes methods, reagents, and kits for the recovery of nucleic acid from reaction mixtures. These embodiments are based on procedures comprising the steps of: (1) preparing a reaction mixture comprising nucleic acid; (2) adding to the reaction mixture a reagent for promoting inactivation of nucleases and precipitation of undigested nucleic acid, the added reagent comprising a chaotropic agent and an alcohol included in a proportion effective to precipitate nucleic acid from the reaction mixture; and (3) precipitating nucleic acids from the reaction mixture.

These reaction mixtures are typically incubated under conditions effecting enzymatic degradation of single-stranded nucleic acid. In more specific embodiments of the invention, the reaction mixture comprises RNA, a ribonucleolytic enzyme effective to digest single-stranded RNA, and a carrier agent that is relatively insensitive to ribonucleolytic degradation. The carrier serves to promote subsequent nucleic acid precipitation, and can comprise, for example, linear acrylamide or DNA fragments. Chaotropic agents are used in some embodiments of the invention. In some preferred embodiments, the chaotropic agents comprise guanidium compounds. For example, guanidium thiocyanate or guanidium chloride are useful chaotropic agents. Exemplary nucleic acid precipitating alcohols are isopropyl alcohol and ethanol.

The methods of the invention also include embodiments where reducing agents, detergents, and/or chelating agents are added to the reaction mixture. Exemplary reducing agents are dithiothreitol and β-mercaptoethanol. Exemplary detergents are N-lauryl sarcosine and sodium dodecylsulfate. EDTA is an example of a chelating agent which may be used in the invention.

In the preferred practice of the method, predetermined optimized amounts of ribonucleases are diluted into an appropriate volume of the first novel reagent described above ("Reagent 1"), and an appropriate volume (usually a 10-fold excess) of the mixture is added to each reaction in the assay series. Reagent 1 contains salts and buffers necessary for the nuclease digestion reaction to proceed, as well as a carrier agent consisting of either linear acrylamide at a concentration of 0.1 mg/ml or sheared high molecular weight DNA at a concentration of 20 μg/ml. The carrier need not be limited to linear acrylamide or DNA, but may be any macromolecule which is resistant to ribonuclease and will promote precipitation of RNA. The buffer may be, but is not limited to HEPES maintained at a pH of 7.5. The salt may be, but is not limited to, sodium acetate present at a concentration of 300 mM.

In a further preferred method, the invention includes the step of inactivating the nucleases (introduced into each reaction at the above step) by the addition to each reaction a second reagent (Reagent 2). Reagent 2 contains a guanidinium compound that effects the denaturation and consequent inactivation of the nuclease in each reaction. Reagent 2 also preferably contains additional agents to aid in the inactivation of nucleases, such as DTT and N-lauroyl sarcosine. Reagent 2 also preferably contains an alcohol such as isopropanol or ethanol in a concentration necessary to effect the precipitation of nucleic acid.

The method will then typically include a further step of incubating the reaction mixtures at reduced temperature (e.g., 4° C. or −20° C. or −80° C.) for an appropriate length of time (e.g., 5 to 60 minutes, particularly 15 minutes) to effect the quantitative precipitation of nucleic acid in the reaction mixtures. This may also include a further step of concentrating the nucleic acid precipitated from each reaction in the above step, e.g., by centrifugation of each reaction for 15 minutes at 12,000×g in a laboratory microfuge. The concentrated nucleic acid in each reaction may then be separated from the supernatant solution, e.g., by aspiration of the supernatant solution from the pelleted nucleic acid, and solubilization of nucleic acid pellets in an appropriate buffer.

In still further embodiments, the present invention concerns kits for carrying out the digestion of single-stranded RNA, and, in particular, to kits adapted for use in connection with ribonuclease protection assays. Kits of the present invention will generally include a container that includes a composition for use in recovering nucleic acid from a reaction mixture. This composition will include a nuclease-resistant carrier agent that is relatively insensitive to degradation by the nucleolytic enzyme. In preferred embodiments, the composition will further include one or more salts, buffers, and ribonucleolytic enzymes. One may find particular advantages by including the necessary salts, buffers and enzyme in the same composition admixture which include the carrier agent. However, this is not a requirement in that the carrier agent may be suitably aliquoted into a separate container such that it may be employed by the end-user.

In more preferred embodiments, the kits of the present invention will include a second container that comprises a mixture for effecting the inactivation of nuclease and promoting precipitation of undigested nucleic acid. Typically, the mixture of the second container will include a guanidinium compound such as guanidinium thiocyanate or guanidinium chloride. Other reagents which may be optionally included in the mixture of the second container include a reducing agent, such as DTT or β-mercaptoethanol, a detergent such as N-lauroyl sarcosine or SDS, or a chelating agent, such as EDTA.

Full advantages of the kits of the present invention will be realized where the mixture of the second container further include an alcohol, such as isopropyl alcohol or ethanol, included in a proportion effective to precipitate nucleic acids from the reaction mixture.

Of course, depending on the degree of self-containment and completeness that one desires for the kits, other materials may be incorporated as well. For example, one may include various hybridization buffers, solutions of yeast or tRNA, loading buffers for carrying out polyacrylamide gel electrophoresis, elution buffers, and even controls, into an appropriate container or containers where desired. Where complete kits of this nature are contemplated, all that must be supplied by the end user will be various pieces of standard laboratory equipment.

DETAILED DESCRIPTION OF THE PREFERRED EMBODIMENTS

The following examples illustrate methodology and particular compositions that represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The most preferred protocol for carrying out the practice of the present invention is set forth in a significant degree of detail in the instruction manual for RPA II™ Ribonuclease Protection Assay Kit (Ambion, Inc., Austin, Tex.). This instruction manual is set forth in the Appendix hereof. The following examples, however, are quite adequate to teach to those of experience in nuclease protection assays, the preferred practice of the invention.

PREPARATION OF REAGENT 1

Example 1

The most preferred embodiment of Reagent 1 is made by combining 100 ml of a 3M stock solution of sodium acetate, maintained at a pH of approximately 7.5 with 10 ml of a 1M stock solution of HEPES buffer (Sigma Chemical Co., P.O. Box 14508, St. Louis, Mo. 63178, U.S.A.; CAT#H3375) maintained at a pH of approximately 7.5 and 10 ml of a 0.5M stock solution of EDTA (Sigma) in a final volume of one liter in distilled $H_2O$. To the resulting solution comprised of 300 mM sodium acetate/10 mM HEPES pH 7.5/5 mM EDTA is added 5 ml of a 2% stock solution of linear acrylamide or 5 ml of a 4 mg/ml stock solution of sheared high molecular weight DNA. The final concentration of linear acrylamide in Reagent 1 is 0.1 mg/ml. The final concentration of the alternative carrier, sheared high molecular weight DNA, is 20 μg/ml. The linear acrylamide stock solution is made by dissolving 2 grams of linear acrylamide (Aldrich Chemical Co., 1001 W. St. Paul Ave., Milwaukee, Wis. 53233, U.S.A., Cat. #18,127-7) in 100 ml of distilled water. Sheared high molecular weight DNA stock solution is made by dissolving about 1 gm of DNA (for example, herring sperm DNA; Sigma Cat. #D6898) in 100 ml of distilled water by prolonged stirring. The DNA is sheared by sonication or other means to an average size of about 2 kilobases.

Example 2

The novel reagent 1 of this invention is also producible by using sodium chloride rather than sodium acetate in the composition described in example 1, at an effective concentration similar to example 1.

Example 3

The novel Reagent 1 of this invention is also producible by using Tris buffer (Sigma) rather than HEPES, in the composition described in example 1, at an effective pH and concentration similar to example 1.

PREPARATION OF REAGENT 2

Example 4

The most preferred embodiment of Reagent 2 is made by combining 158 gm of guanidinium thiocyanate (Sigma, Cat.#G-6639) with 8.3 ml of a 20% solution of N-lauroyl sarcosine (Sigma, Cat#L-5125) in $dH_2O$, and 1.3 gm of dithiothreitol (Boehringer Mannheim, Cat.#709000) in a total volume of 333 ml in distilled water. When all components are dissolved, 667 ml of isopropyl alcohol (ACS) is added and the solution is mixed to homogeneity. The composition of the resulting solution, Reagent 2, is 1.3M guanidinium thiocyanate, 0,167% N-lauroyl sarcosine, 8.3 mM DTT, and 67% isopropyl alcohol. Reagent 2 is stable when stored at room temperature for at least 6 months, and is stable indefinitely when stored at −20° C.

Example 5

The Reagent 2 of this invention is also producible by using guanidinium chloride in place of guanidinium thiocyanate in the composition described in example 5, at an effective concentration similar to example 5.

Example 6

The Reagent 2 of this invention is also producible by omitting the N-lauroyl sarcosine from the composition described in example 5.

Example 7

The Reagent 2 of this invention is also producible by omitting the dithiothreitol from the composition described in example 5.

Example 8

The Reagent 2 of this invention is also producible by using reducing agents other than dithiothreitol, for example β-mercaptoethanol, in the composition described in example 5, at an effective concentration similar to example 5.

Example 9

The Reagent 2 of this invention is also producible by using detergents other than N-lauroyl sarcosine, for example sodium dodecylsulfate, in the composition described in example 5, at an effective concentration similar to example 5.

Example 10

The Reagent 2 of this invention is also producible by using ethanol instead of isopropyl alcohol in the composition described in example 6, at an effective concentration similar to example 5.

PRACTICE OF THE METHOD

Example 11

The most preferred embodiment of the method of this invention is for inactivating ribonucleases and recovering nucleic acid from the reaction mixtures that comprise ribonuclease protection assays. The method of inactivating ribonucleases and recovering nucleic acid from the reaction mixtures employs the novel reagents prepared as shown in examples 1 and 6 (Reagents 1 & 2 respectively).

In the most preferred embodiment of the method of this invention, an approximately 10-fold excess of Reagent 1 containing a predetermined amount of ribonuclease is added to the hybridization reaction that comprises the ribonuclease protection assay reaction mixture at the hybridization step of the assay. After the addition of Reagent 1, the mixture is vortexed, centrifuged briefly, and incubated under appropriate conditions (for example 30 minutes at 37° C.) to permit unhybridized nucleic acid to be degraded by the ribonuclease. After the incubation, an approximately 1.4 fold excess of Reagent 2 is added to each reaction mixture, the mixtures are vortexed briefly, and then stored at lowered temperatures for an appropriate time (for example, 15 minutes at −20° C).

The reaction mixtures are then centrifuged under appropriate conditions (for example, 15 minutes at 12,000 g in a microcentrifuge) in order to collect the precipitated nucleic acid on the bottom and sides of the reaction vessel (this process is known as pelleting the nucleic acid). After centrifugation the supernatant fluid is carefully removed from each reaction vessel by aspiration or decanting, and the pellets are resuspended in an appropriate volume of a suitable buffer (for example, 8 μl of a solution of 80% formamide/0.1% tracking dye), and the nucleic acid recovered in this manner is analyzed by electrophoresis.

OTHER EMBODIMENTS

Other uses of Reagent 1 and Reagent 2, that take advantage of their ability to inactivate nucleases and quantitatively precipitate nucleic acid, are envisioned to be within the scope of this invention. Such uses include, e.g., their use as step-saving and time-saving reagents in S1 nuclease protection assays and other situations in which it is desirable to inactivate nucleases and recover nucleic acid in an undergraded form from in vitro biochemical or molecular biological reactions.

The degree to which reagents such as Reagents 1 and 2 are successful in promoting recovery of undergraded nucleic acid using the method of this invention was studied in ribonuclease protection reactions using 10 μg of mouse liver RNA and $1\times10^5$ cpm of $^{32}P$-labeled antisense RNA corresponding to part of the mouse β-actin gene. Increasing amounts of two ribonucleases were added to the reactions. It was found that omitting the steps for nuclease-inactivation resulted in recovery of the labeled RNA in a degraded form, whereas intact RNA was recovered using either the standard protocol or the method and reagents of this invention.

The main advantages to using the method and reagents of this invention are as follows: 1) Reagent 2 replaces the proteinase K stock solution, SDS stock solution, phenol/chloroform/isoamyl alcohol mixture and ethanol. These reagents are individually prepared and used separately in the conventional procedure. 2) Reagent 2 is a stable reagent containing no labile enzymatic components such as proteinase K whose activity may vary between batches, and thus has an extended, indefinite shelf-life. 3) By eliminating the phenol/chloroform extraction, the method of this invention eliminates the need to transfer the reaction mixture to a new vessel following nuclease inactivation, thereby greatly streamlining the analysis of multiple samples. The entire ribonuclease protection assay procedure is performed in a single microcentrifuge tube and the required number of disposable plastic tubes and pipet tips is decreased to less than half the number used in the conventional method. 4) The use of Reagent 2 in the disclosed method permits the experimental protocol to be modified such that steps that were previously performed sequentially may be done simultaneously, resulting in a significant decrease in the time required to perform the analysis. 5) By eliminating the phenol/$CHCl_3$ extraction, which required close-range manipulation of radioactive reaction mixtures, the use of Reagent 2 in the disclosed method greatly diminishes the exposure of the user of radiation hazards. 6) The use of Reagent 2 as an alternative to phenol/$CHCl_3$ extraction eliminates the need for the special requirements for the disposal of phenol/$CHCl_3$, which are required by law.

Regarding the use of guanidinium compounds and alcohol in standard methods of isolating RNA from biological sources, and the use of these same chemicals in the present invention, a number of differences exist between the use of these chemicals as described in the prior art and in the present invention. For example, in the standard RNA isolation procedure, there is sequential use of guanidinium-containing reagents and alcohol, whereas in the present invention, guanidinium and alcohol are both contained in a single reagent which is used for the simultaneous inactivation of nuclease and precipitation of RNA. Furthermore, the guanidinium concentration in standard RNA isolation methods is high, on the order of 4M–5M, while the guanidinium concentration as used in the preferred embodiment of the present invention is only 0.78M. Also, the alcohol concentration used for RNA precipitation in the standard method is 50–75%, depending on whether isopropanol or ethanol is used, whereas the final alcohol concentration achieved in the preferred embodiment of the method and reagents of this invention is 40%, as isopropanol.

Example 12: Detailed Protocol for Usage

The Ribonuclease Protection Assay (RPA II TM) is an extremely sensitive procedure for the detection and quantitation of RNA species (usually mRNA) in a complex sample mixture of total cellular RNA. For the RPA, a labeled probe is synthesized that is complementary to part of the target RNA to be analyzed. This is most easily done by inserting the probe fragment into one of the common transcription vectors under the control of a bacteriophage promoter (usually the T3, T7, or SP6 promoter) and using the corresponding T3, T7, or SP6 RNA polymerase to generate an RNA probe of high specific activity. The labeled probe is then mixed with the sample RNA and incubated under conditions that favor hybridization of complementary transcripts. After hybridization, the mixture is treated with ribonuclease to degrade single-stranded, unhybridized probe. Labeled probe that hybridized to complementary RNA in the sample mixture will be protected from ribonuclease digestion, and can be separated on a polyacrylamide gel and visualized by autoradiography. When the probe is present in molar excess over the target fragment in the hybridization reaction, the intensity of the protected fragment will be directly proportional to the amount of complementary RNA in the sample mixture.

Compared to hybridization protocols that rely on RNA bound to a solid support (i.e. Northern blots), low abundance mRNA's are detected more readily and quantitated more accurately by using a solution hybridization procedure such as the RPA (Lee and Costlow, 1987). Since the probes used in the RPA are generally significantly shorter than the mRNA species being detected, the target RNA preparation need not be completely intact (breaks in mRNA that occur outside the region that hybridizes to the probe will have no effect on the RPA, but result in band smearing on Northern blots). Due to the high resolution of the acrylamide gel system used to generate the primary data, the RPA assay is well-suited for mapping positions of internal and external junctions in mRNA, for example transcription initiation and termination sites and intron/exon boundaries (Kekule et al., 1990; Melton et al., 1984; Calzone et al., 1987) by adjusting the ribonuclease concentration in the digestion reaction, the assay can be used to detect small differences between the probe and target mRNA. In this way, the RPA can be used to map mutation sites (Myers and Mariatis, 1986; Winter et al., 1985; Genovese et al., 1989; Takahashi et al., 1989). Despite these advantages, ribonuclease protection analysis has not replaced older methods of mRNA detection. This is probably because the RPA is quite template dependent and has a reputation as a difficult assay to set up and optimize. The present invention kit avoids many of the problems and pitfalls associated with ribonuclease protection assays, and to give the user maximum convenience while still allowing sufficient flexibility for optimizing experiments for specific templates.

A. Reagents, Components and Equipment For Detailed Protocol

| | | |
|---|---|---|
| A. | Soln. A | 2.8 ml Hybridization Buffer<br>80% deionized formamide/40 mM PIPES pH 6.4/400 mM NaOAc pH 6.4/1 mM EDTA |
| B. | Soln. Bx | 30 ml RNase digestion buffer (Reagent 1 of Example 1, above) |
| C. | Soln. C | 0.5 ml 5 mg/ml yeast RNA in $dH_2O$ |
| D. | Soln. Dx | 45 ml RNase inactivation/precipitation mixture (Reagent 2 of Example 4) |
| | Caution: | Soln. Dx contains guanidinium thiocyanate, which can pose a health hazard if mishandled. Always wear gloves when handling Soln. Dx and never allow Soln. Dx to come in contact with acids. Acidification of Soln. Dx can release toxic |

-continued

| | | |
|---|---|---|
| | | cyanide gas! |
| E. | Soln. E | 1.5 ml loading buffer: 80% formamide/0.1% xylene cyanol/0.1% bromophenol blue/2 mM EDTA |
| F. | Soln. F | 8 ml Probe elution buffer: 0.5M $NM_4OAc$/1 mM EDTA/0.2% SDS |
| G. | Soln. G. | Positive control templates: 10 ul of a 1:1:1 mixture of three linearized plasmids containing a 250 bp mouse b-actin gene fragment inserted downstream of either the SP6, T3, or T7 phage promoters. Sufficient for 10 transcription reactions. |
| H. | Soln. H | Positive control sample RNA: 60 ug of total mouse liver RNA, at a concentration of 0.5 mg/ml in 0.1 mM EDTA. |
| I. | Soln. T | 500 ul 5,000 units/ml RNase T1 (cloned) |
| J. | Soln. R | 300 ul of a mixture of 50 units/ml RNAse A + 10,000 units/ml RNase T1 (cloned). |
| K. | | DNA template and reagents for preparing radiolabeled RNA probe (see Additional Information section VII-A for details of probe preparation) |
| L. | | Constant temperature incubator or heat block (37° C. and 42°–45° C.) and 90° C. |
| M. | | Microcentrifuge and microcentrifuge tubes. |
| N. | | Adjustable pipettors and tips. |
| O. | | Apparatus and reagents for preparing and running denaturing acrylamide gels (high quality urea, acrylamide and bis-acrylamide, Tris-borate-EDTA buffer, ammonium persulfate, TEMED). |
| P. | | High Quality Ethanol |
| Q. | | −20° C. Freezer. |
| R. | | Pasteur pipets and bulbs. |
| S. | | Disposable gloves. |

B. Protocol For Use of Kit

The Ribonuclease Protection Assay protocol is divided into three parts:

1. Hybridization of Probe and Sample RNA
2. Ribonuclease Digression of Hybridized RNA
3. Separation and Detection of Protected Fragments 1. Hybridization of Probe and Sample RNA In the first step, separate solutions of sample RNA and probe are mixed together and concentrated by ethanol precipitation. The amount of sample RNA required will depend on the abundance of the mRNA being detected and the specific activity of the probe. For quantitative detection of mRNA, it is important that the labeled probe be present in molar excess over the target mRNA. If you have prior information about the abundance of the target mRNA, a calculation can be made to determine how much probe is required to be in 4-fold molar excess. For example, if the target mRNA is abundant (i.e. $\geqq 0.1\%$ of all mRNA), then 10 ug of total cellular RNA would contain about 0.6 fm of the target mRNA, assuming that the target mRNA is 1.5 kb long and that mRNA comprises 3% of total cellular RNA (1 fm$=10^{-15}$ moles). Thus, a four-fold molar excess of a 300 nucleotide probe with a specific activity of $3\times10^8$ cpm/ug would require 2.4 fm or about $7\times10^4$ cpm, corresponding to about 240 pg. If the message is less abundant, or less sample RNA is used in the hybridization reaction, then fewer cpm of probe would be needed. If the probe is longer than 300 nucleotides, or has a specific activity greater than $3\times10^8$ cpm/ug, then more cpm of probe will be needed to achieve 4-fold molar excess.

The appropriate amounts of probe and sample RNA are most accurately transferred by pipetting predetermined volumes of each RNA in aqueous solution. The sample RNA is usually stored at a concentration of 0.1–2.0 mg/ml in DEP (diethlypyrocarbonate)-treated $dH_2O$/0.1 mM EDTA or in 0.5M $NH_4OAc$ (ammonium acetate)/0.1 mM EDTA at −80° C. The probe may be conveniently stored in elution buffer at −80° C. After the appropriate volumes of probe and sample RNA have been mixed together, the salt concentration is adjusted if necessary (for example by adding $NH_4OAc$ to a final concentration of 0.5M), and 2.5 volumes of ethanol are added to co-precipitate the sample and probe RNAs. If the required volumes of probe and sample RNA are very small, on the order of 10 ul or less, they may be concentrated by lyophilization in a microcentrifuge under vacuum (i.e., a speed-vac), as an alternative to ethanol precipitation.

1. Mix predetermined volumes of sample RNA and labeled probe (see above) in a 1.5 ml microcentrifuge tube. A typical experiment might include 20 tubes with different amounts or sources of sample RNA. For each different probe used, include two control tubes of probe with 2 ul of Soln. C (yeast RNA).
2. Place tubes in −20° C. freezer for 15 min.
3. Pellet the RNA's by centrifuging at maximum speed (about 10,000 rpm) for 15 min., preferably at 4° C.
4. Remove the EtOH supernatant, taking care to avoid dislodging the pellets. Caution: The pellets may not adhere tightly to the sides of the microfuge tubes.
5. Dissolve the pellets in 20 ul of Soln. A (hybridization buffer). After adding Soln. A to each pellet, vortex each tube for about 5–10 seconds, then microfuge for a few second to collect the liquid at the bottom of the tube.
6. Incubate tubes at 90°±10° C. for 3–4 minutes to denature the RNA and aid in its solubilization, then re-vortex and re-microfuge briefly.
7. Incubate tubes at 42°–45° C. for about 2–18 hours to allow hybridization of probe and complementary mRNA in the sample RNA. This step can be conveniently done overnight. However, the hybridization time has been successfully reduced to only 2 hours using probe made from the control template included in the kit (Soln. G, labeled to a specific activity of $6\times10^8$ cpm/ug), hybridized with the control sample RNA (Soln. H, mouse liver RNA). The mRNA being detected in Soln. H is for mouse b-actin, which is estimated to comprise 0.02–0.06% of the RNA in liver (Current Protocols in Molecular Biology Vol. I). For the initial detection of an mRNA of unknown abundance, the Inventors recommend overnight hybridization. Hybridization times may be reduced in subsequent experiments depending on the results (i.e. intensity of signal of the protected fragment). However, for accurate quantitation, the hybridization reaction must go essentially to completion. To minimize condensation around the tops of the tubes during hybridization, they should be tightly capped and either incubated in a controlled environment (e.g. a 42° C. incubator), or submerged in a water bath or water-filled heat block, weighted down with a flat object.

2. RNase Digestion of Hybridization Probe and Sample RNA

1. Thaw a bottle of Soln. Bx (RNase digestion buffer) and remove an appropriate volume (200 ul×number of assay tubes), and add the appropriate amount of Soln. R (concentrated RNase A+RNase T1 mixture in glycerol). Typically this is a 1:100 dilution, however, the optimal concentration is template dependent and may need to be determined empirically. If there is any visible precipitate in Soln. R, vortex and spin the tube briefly before removing the aliquot for dilution. Vortex and spin the diluted mixture briefly to assure even dispersion of Soln. R in Soln Bx.

2. After hybridization, the tubes are removed from the incubator or heat block and centrifuged briefly if any condensation is present on the sides or top of the tube. (Centrifugation will probably not be necessary if the hybridization was done in an incubator).
3. To each tube containing sample RNA, and to one of the yeast RNA control tubes, add 200 ul of the diluted RNase mixture. To the other yeast RNA control tube add 200 ul of Soln. Bx (RNase digestion buffer without RNase).
4. Vortex and centrifuge tubes briefly, then incubate at 37° C. for 30 min. to digest unprotected single-stranded RNA. In some cases, a decreased incubation temperature may be desirable.
5. Add 300 ul of Soln. Dx to all tubes. Vortex and spin tubes briefly.
6. Transfer tubes to −20° C. freezer for at least 15 min. It is not necessary to add additional carrier during this precipitation.

3. Separation and Detection of Protected Fragments

1. Prepare an 8M urea polyacrylamide gel. A 5% acrylamide gel will effectively resolve fragments of about 50–1,000 nucleotides. The Inventors typically run 0.75 mm thick gels, 15 cm wide×12 cm long, with 20 wells that are about 4 mm in width.
2. Pellet the precipitated products of the RNase digestions for 15 min. at maximum speed in a microcentrifuge, preferably at 4° C.
3. Remove all supernatant from each tube, again taking care not to dislodge the supernatant pellet. This step is a frequent source of problems. To remove the last traces of supernatant, it is usually necessary to re-centrifuge the tubes for about 10 seconds (room temperature is O.K.) and then withdraw the residual fluid with a drawn-out Pasteur pipette.
4. Resuspend the pellets in about 8 ul of Soln. E (loading buffer). Tubes should be vortexed for about 5 sec. and briefly centrifuged after adding the loading buffer.
5. Heat the tubes for 3–4 minutes at 90°±10° C. to completely solubilize and denature the RNA. Vortex and microfuge again briefly.
6. Load each sample on the gel and run at about 250 volts (150–300 volts is acceptable for an appropriate length of time to resolve the protected fragment(s). The optimum time will vary depending on the size of the protected fragment but the Inventors typically run the gels until the leading dye band (bromophenol blue) is near the bottom of the gel. It may be desirable to load a smaller portion (for example 1–2 ul) of the yeast RNA control reaction to which Soln. Bx was added. This tube should contain undergraded probe and will have a much stronger signal which can obscure data in adjacent lanes.
7. Transfer the gel to chromatography paper, mark the origins and orientation of lanes, cover with plastic wrap, and expose to X-ray film for an appropriate length of time. The Inventors usually expose overnight-several days using single-side coated X-ray film (e.g. Kodak XRP) without an intensifying screen, or from several hours-overnight with a screen. Expose at −80° C. when screens are used. The gel can be re-exposed several times if necessary after allowing it to warm up to room temperature and wiping off condensation moisture. The gel should be stored at −80° C. if not re-exposed immediately. Users may prefer to dry down thicker gels onto chromatography paper; the Inventors do not find it necessary to dry standard 0.75 mm thick gels.

C. Optimizing Reaction Conditions

1. Suggested Pilot Experiments

The following experiments are suggested to help the new user determine the appropriate amount of sample RNA and probe to use to achieve optimal results in the absence of prior knowledge about the abundance of the target mRNA being detected. The Inventors recommend that the RPA be tried with a range of input sample RNA, using a constant amount of medium-high specific activity probe. Also, to optimize conditions for the RNase digestion, the Inventors suggest varying the concentration of the RNase mixture and determining whether RNase T1 alone offers any advantages. If the sample RNA is in short supply, users may want to modify and scale back these experiments to conserve sample RNA. The details of the pilot experiment, including synthesis and use of the positive control probe and expected results, are shown in Table 1. Table 2 outlines the protocol for making the RNase dilutions.

TABLE 1

| | Suggested Pilot Experiment | | |
|---|---|---|---|
| Tube | Amount sample RNA | Amount Probe[1] | RNase Dilution (Soln. R)[2] |
| 1 | 1.25 ug | $9 \times 10^4$ cpm = 3 fm | 1:100 |
| 2 | 2.5 ug | $9 \times 10^4$ cpm = 3 fm | 1:100 |
| 3 | 5 ug | $9 \times 10^4$ cpm = 3 fm | 1:100 |
| 4 | 10 ug | $9 \times 10^4$ cpm = 3 fm | 1:100 |
| 5 | 10 ug | $9 \times 10^4$ cpm = 3 fm | 1:50 |
| 6 | 10 ug | $9 \times 10^4$ cpm = 3 fm | 1:100 |
| 7 | 10 ug | $9 \times 10^4$ cpm = 3 fm | 1:300 |
| 8 | 10 ug | $9 \times 10^4$ cpm = 3 fm | 1:1000 |
| 9 | 10 ug | $9 \times 10^4$ cpm = 3 fm | 1:50 (Soln. T) |
| 10 | 2 ul Soln. C (yeast RNA) | $9 \times 10^4$ cpm = 3 fm | 1:100 |
| 11 | 2 ul Soln. C | $9 \times 10^4$ cpm = 3 fm | 1:1000 |
| 12 | 2 ul Soln. C | $9 \times 10^4$ cpm = 3 fm | Soln. Bx only/No RNase control |
| 13 | 20 ul = 10 ug Soln. H | $6 \times 10^4$ cpm of control | 1:100 |
| 14 | 2 ul Soln. C | transcript[3] control | 1:100 |

TABLE 1-continued

| | Suggested Pilot Experiment | | |
|---|---|---|---|
| Tube | Amount sample RNA | Amount Probe[1] | RNase Dilution (Soln. R)[2] |
| 15 | 2 ul Soln. C | transcript[3] control | Soln. Bx only/No RNase control |

1) This example is for a 300 nucleotide transcript, labeled to a specific activity of approximately 3 × $10^2$ cpm/ug. If the probe is longer or shorter than 300 nucleotide, more or less cmp will be required to achieve 3 fm. To make a probe with a specific activity of 2.7 × $10^2$ cpm/ug, use 2 ul of $^{32}P$—UIP or $^{32}P$—CIP (800 Ci/mM, 10 mCi/ml) in a 200 ul transcription reaction that contains a 5 uM concentration of unlabeled UIP or CIP.
2) 200 ul to be added to all tubes in step B.3
3) The probe for the control reaction is made by transcribing 1 ul of Soln. G in a 10 ul transcription reaction containing 2-3 ul of $^{32}P$—UIP or $^{32}P$—CIP (800 Ci/mM, 10 mCi/ml) and 3-5 uM concentration of unlabeled UIP or CIP, using 10 units of SP6, T3, or T7 RNA polymerase. This will generate a runoff transcript of about 300 nucleotides (the T3 polymerase-generated transcript is slightly longer), of which 250 nucleotides will be protected by the beta-actin mRNA in Soln. H (mouse liver RNA).

TABLE 2

| | Preparation of RNase Dilutions | | |
|---|---|---|---|
| Dilution | Total Amount Needed[1] | Amount RNase A/T1 mixture | Amount Soln. Bx |
| 1:50 | 220 ul | 4.4 ul Soln. R | 215.6 ul |
| 1:100 | 1.9 ml | 19 ul Soln. R | 1.88 ml |
| 1:300 | 365 ul | 122 ul of 1:100 diln. | 243 ul |
| 1:1000 | 440 ul | 132 ul of 1:300 diln. | 308 ul |

1) Calculated volumes were increased by 10% to allow for pipetting losses. For dilution of Soln. T: Add 4.4 ul Soln. T to 218 ul Soln. Bx.

2. Interpretation of Results

Expose the gel from the pilot RPA experiment overnight with an intensifying screen at −80° C. (The gel may be re-exposed several times if necessary after allowing it to warm up to room temperature and wiping off moisture due to condensation). The autoradiograph should show a band of the appropriate size, representing the major protected fragment, from the samples in Tubes 1 to 4. The band should not be present in the yeast RNA control sample that was digested with RNase (Tube 10). If the intensity of the major protected fragment in the RPA autoradiograph increases with increasing input RNA, then the probe was present in a molar excess over the mRNA in all the reactions, and the amount of probe could confidently be decreased (with all but the highest amount of sample RNA) by a factor of two while still remaining in probe excess in subsequent reactions. Decreasing the probe amount may improve the signal-to-noise ratio and help to eliminate unwanted background. If the intensity of the major protected fragment reaches a maximum at some point in the series of 4 initial reactions, then the probe was no longer in molar excess in those reactions having a signal of the same intensity as in reactions with less input RNA. Such a result indicates that the mRNA is abundant, and that an acceptable signal can be obtained with less input target RNA or with a probe of lower specific activity. Comparison of the signals from the samples in tubes 4 and 6 (which are from identical reactions) will indicate whether reproducibility in the assay is a problem.

If the signal is very weak or absent, even in the reaction with the highest amount of input RNA, the message may be very rare. In this case, the sensitivity of the assay can be increased by increasing the specific activity of the probe. Using ul of $^{32}P$-UTP (at 800 Ci/mmole, 10 mCi/ml) in a 20 ul transcription reaction, and omitting the unlabeled UTP, will result in the synthesis of a probe with a specific activity of approximately $1.3 \times 10^9$ cpm/ug. however, since the UTP concentration in such a reaction would only be 3.75 uM, difficulty in synthesis of full-length transcripts may be encountered, especially for longer probes. Quantitative results require that the probe be present in molar excess over the target mRNA. However, vast excess of probe can result in high background. Other ways to increase the sensitivity of the assay are to use more sample RNA, up to about 20-25 ug per hybridization reaction, to use poly(A) selected mRNA, or to sue a longer probe.

Other potential reasons for failure to see a signal are severe degradation of the sample RNA (which can be checked by using another probe for a reasonably abundant mRNA as an internal standard, or by running the sample RNA on a denaturing agarose gel and looking for degradation of the ribosomal RNA bands), or accidental transcription of the "wrong strand" of the template DNA in the probe synthesis reaction. (In order to make an mRNA complementary "anti-sense" probe, the template should be linearized on the side of the insert that encodes the amino-terminal side of the protein, i.e. on the 5' side of the gene). The Inventors have one report that autoclaving of siliconized tubes resulted in a high pH residue which degraded RNA. Another potential source of probe-related problems is aberrations generated during subcloning. In one case, a probe showed the expected result when used for a Norther blot but protected a fragment in the RPA that was not of the predicted size. Subsequent sequencing of the probe showed that it had undergone rearrangement during subcloning. In another case, sequencing of an intractable probe revealed that the template had undergone a rearrangement that resulted in the wrong strand being transcribed. Of course, it is possible that an absence of signal is a legitimate result due to the gene of interest not being expressed or being rapidly degraded in the tissue or organism being examined. To confirm this possibility, the RPA should be repeated along with an assay of a separate sample RNA prep known to contain detectable levels of the mRNA, or with in vitro synthesized sense-strand mRNA added to the RNA samples, to serve as a positive control. Technical difficulties in performing the assay can be ruled out by successfully completing the positive control reaction provided in the kit. (See Table 1 for information on setting up the positive control reaction). The positive control reaction (tube 13) lane should show a protected band of 250 nucleotides, which should be absent from the control yeast RNA lane from Tube 14. Molecular size markers are conveniently made by end-labeling Sau3A restriction fragments of pUC19 with c-[$^{32}$P]ATP, using polynucleotide kinase. The integrity of the probes used in the pilot experiment is assessed by examining the samples from Tubes 12 and 15. Poor results seen in the context of a degraded probe indicate problems with probe synthesis, purification, or stability..

A common result in an RPA autoradiograph is to see an intense, discrete band representing the major protected fragment, plus an array of less intense, more diffuse, usually smaller "background" bands of unknown origin (for some publications with figures that illustrate this point, see references Whitmore, et al., 1898; Roller, et al., 1989; Tanaka, et al., 1988). Usually the present of some background bands does not detract from the validity of the assay or interfere with its interpretation, but it may nonetheless be desirable to eliminate as much background as possible. One approach to reduce background is to vary the concentration of ribonuclease in the second part of the assay. In the second set of pilot reactions (Tubes 5–12) the concentration and specificity of ribonuclease were varied to optimize the signal to noise ratio and extent of probe/target mismatch detection (if applicable) in the RPA. Although most probe/target mRNA combinations will give acceptable, even identical, results when digested with RNase concentrations that vary over at least a 10-fold range, some templates may require fine-tuning of RNase digestion conditions to adjust the signal to noise ratio and extent of mismatch detection. (When the RNase concentration is decreased, the yeast RNA control reaction should be digested with the lowest concentration of RNase used, to assure validity of the experimental results. If the sample from Tube 11 shows undigested probe, then the low concentration of RNase was not sufficient to completely digest unhybridized probe. Usually this is not a problem, even when the RNase concentration is decreased by more than 10-fold). The results of Tubes 5 to 12 should give an indication of whether "high-end" RNase concentrations will suppress unwanted background without causing an unacceptable level of degradation of the protected fragment, or whether conversely, as is sometimes observed, "low-end" RNase concentrations result in a reduced background. Some investigators will want to use higher concentrations of RNase to maximize recognition of small differences between the probe and sample RNA (for example in the detection of gene transcripts with mutations), while others will want to minimize RNase cleavage at mismatch positions. Another variable relating to RNase digestion is the specificity of the ribonuclease. RNase A cleaves 3′ to cytosine and uridine residues, while RNase T1 cleaves 3′ to guanosine in RNA. If the probe/mRNA hybrid is extremely A+U rich, as is frequently encountered in 3′ untranslated regions of mRNA, "breathing," or transient strand separation may occur, which results in cleavage in double stranded regions. This can be compensated for by lowering the temperature of the RNase digestion step, or more conveniently, by substituting Soln. T ("RNase T1 only") included in the kit for Soln. R. The results of the pilot assay from Tube 9 will give an indication of whether digestion with RNase T1 only offers any advantages.

It is possible that changing the ribonuclease digestion conditions will have no effect on the background. RNase-independent background may be due to properties of the probe, for example contamination with labeled transcripts from the opposite strand or with undergraded template DNA. Reducing the amount and/or the specific activity of the probe to the minimum levels required for detection of the protected fragment may improve the background in some cases.

Another parameter of the RPA protocol that can be altered for optimization of results is the temperature of the hybridization and RNase digestion reactions. In the inventors experience, this variable is less conveniently and less effectively varied than those mentioned already, but it may be worthwhile to investigate it in special cases.

Example 13: Preparation and Purification of Radiolabeled RNA Probe

A preliminary requirement for a ribonuclease protection experiment is synthesis of the radioactive antisense RNA transcript which is used as a hybridization probe for detection of the mRNA of interest. The success of the experiment is critically dependent on the quality of the probe, and the inventors offer the following advise on its preparation and purification.

1. One consideration is probe size. Although probe lengths ranging from 50 nucleotides to over 1000 nucleotides have been used successfully, the inventors suggest 200–500 nucleotides as optimum probe size. (In many cases, an insert can be linearized internally to generate a shorter probe without subcloning). Minimizing probe size helps to maximize synthesis of full length transcripts. Also, the shorter the probe, the more tolerant the assay is of partially degraded sample RNA. However, the shorter the probe, the less sensitive the assay will be. Also, difficulty may be encountered in precipitation of very short probes (i.e. less than 200 nucleotides). It is helpful for the probe to be somewhat longer (in the range of 15–25%) than the protected fragment so that an obvious difference in size is seen between the full-length, undigested probe and the protected product of RNase digestion.
2. Standard protocols for in vitro transcription from bacteriophage promoters may be found in most manuals of molecular biology methods (Melton et al., 1984; Ausubel et al., 1987; Nolan, 1989). These protocols are basically similar, but may vary slightly in the recommended concentrations of nucleotide triphosphates, time and temperature of reaction, reaction volume, and method of purification of the labeled transcript. In vitro Transcription Kits fro probe synthesis are available from Ambion (Catalog #1310–1326). Standard reactions include three unlabeled ribonucleotides, each at a concentration of 500 uM, and a fourth added to a concentration of approximately 3 uM as radioactive ribonucleotide. The radioisotope is typically added as 1–5 ul of tricine-buffered $^{32}$P-UTP or $^{32}$P-CTP (800 Ci/mmole, 10 mCi/ml). The concentration of the limiting nucleotide should be ≧3 uM for most transcripts. For longer transcripts (>300 nucleotides) higher concentrations of limiting nucleotide (5–25 uM) may be required. The increased sensitivity with increased length of hybridizing sequence will tend to offset the decrease in the specific activity of longer probes synthesized in the presence of higher concentrations of unlabeled limiting nucleotide. The proportion of transcripts that are full-length may be maximized by carrying out the transcription reaction at room temperature or 4° C., instead of the commonly recommended 37° C. (20). The reaction volume should be kept as small as possible (10–20 ul) in order to maximize the molar concentration of radiolabeled ribonucleotide and to facilitate probe purification by gel electrophoresis.

3. It is important that the DNA template be destroyed after the RNA transcription reaction by the addition of RNase I (Ambion Catalog #2222). Use 1 unit per reaction; incubate for 15 minutes at 37° C. The gel purification step by itself is not sufficient to remove DNA template that can cause spurious background bands (Kreig, 1990).
4. At the end of the DNase I incubation, an equal volume of gel loading buffer (Soln. E) is added to the reaction, and the tube is heated for 3–5 minutes at 80°–90° C. An aliquot of this final reaction (approximately 2 ul) is removed and diluted for TCA precipitation to determine the specific activity of the radiolabeled product.
5. The Inventors generally recommend that probe be gel purified. The presence of less than full-length probe will result in the appearance of "background" smears and bands. Gel purification has the advantage over other purification methods of resolving full length from shorter transcription products, so that the probe is recovered free from prematurely terminated transcripts as well as unincorporated label. However, if most of your transcript (on the order of 90%) is present as a single band of the expected size, as assessed on a gel, it is probably not necessary to gel purify the probe. The amount of full-length probe can often be maximized by using higher concentrations of limiting nucleotide. When using non-gel purified probe, the proportion of radiolabel incorporated into transcript should be determined by trichloroacetic acid (TCA) precipitation in order to determine how many cpm of the transcription reaction is needed to achieve probe excess. The Inventors recommend that you gel purify probe the first time you use the kit and with new probes or probes which are giving high background.

To gel purify probe, load all or part of the remaining reaction on a 0.75 mm thick 8M urea 5% acrylamide gel and run for about 20 minutes–1 hour at 100–300 volts. After electrophoresis the gel is covered with plastic wrap and exposed to X-ray film for about 5–10 minutes. During exposure, a designated corner (e.g. bottom right) of the film is bent up for orientation, and the film is taped to the plastic-wrapped gel to prevent slipping. Also, lines are drawn with a felt-tip pen across the corners and sides of the film, extending from the film to the glass plate. After exposure, the film is developed and used to precisely localize the area of the gel that contains the full-length labeled transcript, which is usually seen as the most slowly migrating, most intense band on the autoradiograph. The film is aligned with the gel via the bent corner and felt-tip pen marks and lightly taped in place. The gel and film are then inverted so that the position of the probe band on the film can be circled with a felt-tip pend on the back of the glass plate. When the gel is turned back over and the film removed, the area of the gel indicated by the circled region on the glass plate is excised with a razor blade or scalpel, transferred with clean forceps to a microfuge tube, and submerged (by brief vortexing and centrifuging) in about 350 ul of elution buffer (provided in the kit, Soln. F.). Incubate the tube at 37° C. A sufficient amount of labeled probe will have usually been eluted after about two hours to set up many hybridization reactions; however, for the sake of convenience or to maximize recovery of probe from the gel, the incubation can be continued overnight. After overnight incubation, about 95% of the label will typically have diffused out of the gel into the surrounding elution buffer. The amount of radioactive label in an aliquot of the eluted probe is determined in a scintillation counter, and the gel fragment is removed with clean forceps. The probe is typically stored at −20° C. or −80° in elution buffer. Probe stored as aqueous solution (i.e. in elution buffer) is more accurately pipetted than when stored as an ethanol suspension. If accurate measurement is not important, the probe may be stored in 2.5 volumes of ethanol.

Example 14: Precipitation and Storage of RNA

The ribonuclease protection protocol includes two steps which necessitate precipitation: the initial step, when probe and sample RNA's are co-precipitated; and the last step, when the protected fragments are recovered. The inventors offer the following suggestions for precipitation and storage of RNA.

1. To precipitate efficiently from EtOH, the RNA solution requires a minimum concentration of monovalent cations (Wallace, 1987). This requirement is met for the RNA probe when it is stored in elution buffer. If the concentration of salt in the sample RNA solution is low (i.e. less than 0.2M NaCl or 0.5M $NH_4OAc$), the Inventors suggest adding $NH_4OAc$ to a final concentration of 0.5M before addition of 2.5 volumes of ethanol, or to 0.145M if the RNA is already in EtOH. The salt and carrier requirement for the second precipitation is met by the reagents provided in the kit.
2. After adjusting the salt concentration, the RNA is precipitated by addition of 2.5 volumes of EtOH. The RNA-EtOH solutions are then chilled for at least 15 min. at −20° C.
3. To recover the RNA, centrifuge the samples for 15 min. at maximum speed (10,000 rpm) in a microcentrifuge. Ideally, the centrifuge should be refrigerated or located in a 4° C. cold room. All tubes should be positioned the same way during the spin, with the hinges on the attached lids facing away from the center of rotation. The pellets will then form at the back of the tubes, directly below the hinges.
4. RNA pellets do not adhere tightly to the walls of standard polypropylene microcentrifuge tubes, and great care must be taken to avoid losing them when removing the supernatant after centrifugation. The best way to remove the supernatant is by gentle aspiration with a small bulb and a drawn-out Pasteur pipet. Heat the pipet over a bunsen burner flame near the tip until the glass becomes soft enough to pull out with a metal forceps to about the diameter of a thin wire. Snap off the pipet at the constriction, attach the bulb, and gently aspirate off the fluid, keeping the piper opening just below the liquid surface and sliding it down the wall of the tube on the opposite side from where the pellet has formed. When most of the supernatant has been removed, the tube may be re-spun for a few seconds at room temperature, and all residual fluid withdrawn. This "two-stage spin" is usually necessary to remove all traces of liquid when the starting volume of the solution is more than about 200 ul, because about 10–20 ul will adhere to the walls of the tube during aspiration. The RNA pellets recovered in this manner do not require further drying. The Inventors caution against using a vacuum aspirator to remove supernatant from RNA pellets along with the supernatant. An alternative method for removing the supernatant is to carefully pour it off, in one smooth motion, from the opposite side of the tube from where the pellet was formed. The rim of the inverted tube should be blotted into absorbent paper, drained for a few minutes and re-blotted, and then dried upright in a 42° C. incubator for about 15 minutes. This method runs a greater risk of losing the RNA pellets and is not as efficient for removing all traces of liquid.

5. The Inventors have found that substantial errors in quantitation of RNA are introduced when the calculated volumes of RNA are removed by pipetting from EtOH suspension. This is probably due to the formation of RNA aggregates in ETOH. Accuracy is greatly improved by measuring the desired volumes of RNA in aqueous solution. The solutions can be aliquoted in small volumes to minimize freeze/thaw cycles, and stored for reasonably long periods, on the order of a year, at −80° C., with little or no degradation. For the sake of convenience, the Inventors store sample RNA for short-term use in 0.5M $NH_4OAc$, so that it can be precipitated in the first step of the RPA by just adding EtOH. If the goal of the experiment is merely the detection and not the quantitation of mRNA, ethanol suspensions of the probe and/or sample RNA may be pipetted after thorough mixing.

Example 15: Quantitation of mRNA

Several different protocols exist for determining the abundance of a particular mRNA in a heterogeneous sample RNA mixture (Lee, et al., 1987; Roller, et al., 1989). The preferred approach is based on construction of a standard curve, using known amounts of in vitro synthesized sense-strand RNA hybridized with an excess of $^{32}P$-labeled antisense probe. Hybridization reactions containing various amounts of the sample RNA mixture are analyzed in conjunction with the reactions used to generate the standard curve. The intensity of probe fragments protected by the different amounts of sample RNA is compared to the standard curve and used to define absolute amount of the protecting RNA species in the sample RNA.

The sense-strand transcripts used for calibration of the assay can be made by linearizing the DNA template used for antisense probe synthesis on the other side of the probe insert, and synthesizing transcript from the opposite strand, provided the insert is flanked by opposable promoters. Quantitation of the sense-strand transcript is most easily accomplished by including a $^{3}H$-ribonucleotide as tracer. The position of the full-length $^{3}H$-labeled transcript on the probe purification gel is deduced by comparison to the position of the same-sized $^{32}P$-labeled antisense transcript run in an adjacent lane of the gel. (The lower energy $^{3}H$ isotope will not make a visible signal on the X-ray film unless fluorographic techniques are used, but these would render the $^{3}H$-transcript unsuitable for use in the hybridization reactions.) Following synthesis, the specific activity and yield of $^{3}H$-transcript are determined by counting an aliquot of the reaction in an appropriate fluor-containing scintillation cocktail. Using 4 ul of $^{3}H$-CTP (30 Ci/mM, 1 mCi/ml concentration) in a 20 ul transcription reaction will result in synthesis of a transcript with a specific activity of about $5\times10^{7}$ cpm/ug. (Addition of cold CTP may not be needed since the $^{3}H$-CTP will be present at 6.7 uM.) Since the specific activity is known, the molar amount of sense strand can be calculated based on the sized of the in vitro transcript. If the protected fragment in the sample RNA is the same size as the sense strand used to generate the standard curve, equivalent intensities between the standard curve and the sample RNA indicated equimolar amounts of protecting RNA (mRNA or sense strand transcript). If the sizes of the protected fragments differ, the molar amounts will differ in proportion to the sizes of the protected fragments. Also, the intensities of the different-sized protected bands will differ proportionally. The assay can be quantitated by densitometric scanning of the autoradiograph, or by excising and counting the protected fragments (Roller, et al., 1989; Hershey, et al., 1989). Alternatively, the standard curve can be constructed by TCA precipitating and counting the protected species (Lee, et al., 1987). For some purposes, precise quantitation may not be necessary, especially when the amount of $^{3}H$-sense strand in the calibration reactions is varied in small increments. Conversion of molar or mass amounts of protecting mRNA in the total RNA sample into number of transcripts per cell requires knowledge of the number of cells used to prepare the sample RNA. Detailed description for the quantitation of cell number can be found in Lee, et al., 1987.

Example 16: Mapping RNA

Because of its high sensitivity and resolution, the RPA procedure is well suited for mapping internal and external boundaries in mRNA. The basic requirement for mapping using RPA analysis is that the probe span the region to be mapped. This usually means that the probe is derived from a genomic clone, as opposed to a cDNA clone. For example, in order to map the transcription initiation site for a given mRNA, a probe is prepared by subcloning and transcribing a genomic fragment that extends from upstream of the gene of interest to some point in the first exon. Probe synthesis, purification, hybridization, and RNase digestion are carried out using the standard RPA protocol. The transcription start site is mapped by comparing the size of the protected fragment is 75 nucleotides shorter than the probe, the transcription start site would lie 75 nucleotides downstream from the 3′ end of the probe. For exact determination of the size of the protected fragment (necessary to map the transcription start site to the single nucleotide level), the protected fragment may be resolved on a sequencing gel in conjunction with a DNA "sequencing ladder" reaction. (The relative mobilities of RNA and DNA fragments in 7M urea acrylamide gels differ by approximately 5–10%, depending on the particular electrophoresis parameters chosen (Molecular Cloning, A Laboratory Manual, 2nd Ed., 1989), with RNA fragments running somewhat slower than their DNA counterparts.) If such a high degree of resolution is not required, adequate molecular size markers may be prepared by end-labeling DNA fragments generated by digestion of a plasmid with a frequent-cutting restriction enzyme. More detailed information on using the RPA procedure for mapping may be found in refs. (Melton, et al., 1984; Calzone, et al., 1987; Takahashi, et al., 1989; and Zinn, et al., 1983).

The foregoing examples illustrate methodology and particular compositions that represent laboratory techniques discovered by the inventors to function well in the practice of the invention, and thus can be considered to constitute preferred modes for its practice. Moreover, it should appreciated that the invention will be applicable generally to a variety of reactions where one desires to recover nucleic acids. Thus, its applicability is not limited to use in connection with ribonuclease protection assays. Additionally, those of skill in the art should, in light of the present disclosure, appreciate that many changes can be made in the specific embodiments which are disclosed and still obtain a like or similar result without departing from the spirit and scope of the invention.

REFERENCES

The disclosures of the following references, as well as those set forth in the attached Appendix, to the extent that they supplement or expand upon methods and compositions disclosed herein, are hereby incorporated by reference.

Ausbel, et al., *Current Protocols in Molecular Biology,* Wiley Interscience, Vol. 1, p 4.2.3, 1987

Chomczynski, et al., *Anal. Biochem.,* 162:156–159, 1987

Sambrook, et al., *Molecular Cloning: A Laboratory Manual, Second Edition,* Cold Spring Harbor Laboratory Press, pp. 7.75–7.76, 1989

Lee, J. J. and Costlow, N. A. 1987. Methods in Enzymology 152:633–648.

Kekule, A. S., et al. 1990. Nature 343:457–461

Melton, D. A., et al. 1984. Nucleic Acids Res. 12:7035–7056.

Calzone, F. et al., 1987. Methods in Enzymology 152:611–632.

Myers, R. M. and Mariatis, T. 1986. Cold Spring Harbor Symposia on Quantitative Biology Vol. LI:275–284.

Winter, E. et al., 1985. Proc. National Academy of Science 82:7575.

Genovese, C., et al., 1989. Journal of Biological Chemistry 264:9632–9637.

Takahashi, T., et al., 1989. Science 246:491–496.

Whittemore, L. A., and Maniatis, T. 1989. Molecular Cell Biology 64:1329–1337.

Roller, R. J., et al., 1989. Development 106:251–261.

Tanaka, M., et al., 1988. Genes and Development 2:1764–1778.

Current Protocols in Molecular Biology Vol. I pp 3.8.1–3.8.4 (1987) edit. Ausubel et al., Massachusetts General Hospital, Harvard Medical School.

Molecular Cloning, A Laboratory Manual, 2nd edition pp. 10.27–10.37 (1989) edit. C. Nolan, Cold Spring Harbor Laboratory Press.

Myers, R. M., et al., 1985. Science 230:1242–1246.

Wallace, D. M., 1987. Methods of Enzymology 152:41–46.

Hershey, A. D., et al., 1989. Science 247:960–962.

Zinn, K., et al., 1983. Cell 34:865–879.

Zinn, K., et al., 1988. Science 240:210–212.

Lorenz, L. J., et al., 1989. Development 107:869–880.

Krieg, Paul A., 1990. Nucleic Acids Res. 18:6463

Krieg, Paul in Methods in Gene Technology Vol. I, edit, J. W. Dale and P. G. Sanders. 1990, J.A.I. Press (in press).

What is claimed is:

1. A method for the recovery of nucleic acid from a reaction mixture comprising:

preparing a reaction mixture comprising RNA, a nuclease effective to digest single-stranded RNA, and a nucleic acid precipitating carrier agent at a concentration effective to assist in the precipitation of undigested RNA;

incubating the reaction mixture under conditions effecting enzymatic degradation of single-stranded nucleic acid;

adding to the reaction mixture a reagent comprising a nuclease inactivating chaotropic agent in a concentration sufficient to inactivate the nuclease and a nucleic acid precipitating alcohol in a concentration sufficient to precipitate undigested RNA; and inactivating the nuclease while essentially simultaneously precipitating nucleic acids from the reaction mixture without organic extraction of proteins from the reaction mixture.

2. The method of claim 1 wherein the carrier agent comprises linear acrylamide.

3. The method of claim 1 wherein the carrier agent comprises DNA fragments.

4. The method of claim 1 wherein the chaotropic agent comprises a guanidinium compound.

5. The method of claim 4 wherein the guanidinium compound comprises guanidinium thiocyanate or guanidinium HCl.

6. The method of claim 1 wherein the added reagent further comprises a nuclease inactivation enhancing reducing agent in a concentration sufficient to assist in the inactivation of the nuclease.

7. The method of claim 6 wherein the reducing agent comprises mercaptoethanol or dithiothreitol.

8. The method of claim 1 wherein the added reagent further comprises a nuclease inactivation enhancing detergent in a concentration sufficient to promote in the inactivation of the nuclease.

9. The method of claim 8 wherein the nuclease inactivation enhancing detergent is SDS or N-lauroyl sarcosine.

10. The method of claim 1 wherein the alcohol comprises isopropyl alcohol or ethanol.

11. The method of claim 1 wherein the precipitated nucleic acid is separated by centrifugation or filtration.

12. The method of claim 1 wherein the reaction mixture comprises nuclease A, T1, S1 or RNase I from *E. coli.*

13. The methods of claim 12 wherein the reaction mixture comprises nuclease A or T1.

* * * * *